(12) United States Patent
Kline

(10) Patent No.: US 8,826,913 B2
(45) Date of Patent: Sep. 9, 2014

(54) DENTAL APPLIANCE

(76) Inventor: John C. Kline, Akron, OH (US)

(*) Notice: Subject to any disclaimer, the term of this patent is extended or adjusted under 35 U.S.C. 154(b) by 95 days.

(21) Appl. No.: 13/208,476

(22) Filed: Aug. 12, 2011

(65) Prior Publication Data
US 2013/0040266 A1 Feb. 14, 2013

(51) Int. Cl.
A61F 5/14 (2006.01)
A61F 5/56 (2006.01)

(52) U.S. Cl.
CPC ........... A61F 5/566 (2013.01); A61F 2005/563 (2013.01)
USPC ........................................................ 128/861

(58) Field of Classification Search
CPC ............. A61F 5/56; A61F 5/566; A61C 5/14; A61C 19/04; A61C 5/045
USPC ................ 128/848, 859, 861; 602/902; 433/6
See application file for complete search history.

(56) References Cited

U.S. PATENT DOCUMENTS

| | | | |
|---|---|---|---|
| 3,813,781 A | 6/1974 | Forgione | |
| 4,304,227 A * | 12/1981 | Samelson | 128/848 |
| 4,848,365 A * | 7/1989 | Guarlotti et al. | 128/859 |
| 5,083,770 A * | 1/1992 | Holland | 472/70 |
| 5,277,202 A * | 1/1994 | Hays | 128/848 |
| 5,339,832 A * | 8/1994 | Kittelsen et al. | 128/862 |
| 5,513,656 A | 5/1996 | Boyd, Sr. | |
| 5,547,381 A * | 8/1996 | Nutting | 433/219 |
| 5,562,106 A * | 10/1996 | Heeke et al. | 128/848 |
| 5,911,576 A * | 6/1999 | Ulrich et al. | 433/68 |
| 6,302,686 B1 | 10/2001 | Chott et al. | |
| 6,491,521 B1 * | 12/2002 | Fowler, Jr. | 433/167 |
| 6,830,051 B1 | 12/2004 | Lesniak et al. | |
| 7,234,467 B2 | 6/2007 | Ball | |
| 7,490,609 B2 | 2/2009 | Brown | |
| 7,556,044 B2 | 7/2009 | Ball | |
| 7,637,262 B2 | 12/2009 | Bailey | |
| 7,658,193 B2 | 2/2010 | Lesniak | |
| 7,832,404 B2 | 11/2010 | Jansheski | |
| 7,890,193 B2 | 2/2011 | Tingey | |
| 8,459,267 B2 * | 6/2013 | Zimmerman | 128/861 |
| 2003/0116164 A1 | 6/2003 | Boyd, Sr. | |
| 2005/0284489 A1 * | 12/2005 | Ambis, Jr. | 128/859 |
| 2013/0146067 A1 * | 6/2013 | Tschackert | 128/861 |

* cited by examiner

Primary Examiner — Patricia Bianco
Assistant Examiner — Camtu Nguyen
(74) Attorney, Agent, or Firm — Roger D. Emerson; Timothy D. Bennett; Emerson Thomson Bennett

(57) ABSTRACT

A dental appliance may have an incisor reception zone and first and second canine reception zones. The top portions of the canine reception zones may have a greater thickness that the top portion of the incisor reception zone. The top portions of the canine reception zones may also be elastic.

14 Claims, 8 Drawing Sheets

DENTAL APPLIANCE

I. BACKGROUND

A. Field of Invention

This invention relates generally to methods and apparatuses related to dentistry and more specifically to methods and apparatuses related to the treatment of bruxism.

B. Description of the Related Art

Bruxism is commonly known as clenching, bracing, gnashing, and or grinding of one's teeth. Stress and tension are reported as major contributors in the etiology of this condition although many theories exist as to its cause.

The problem and dispute arises as to the cause of the rampant parafunctional habits and parafunctional muscular activity found in most human population. The prevalence of excessively worn dentitions (including primary teeth of young children) appears to indicate that there is excessive muscular activity that is over riding any natural "cuspid protected" scheme that nature has provided. The exact cause of such muscular over activity and tension is presently unknown, however the stress of daily life seems to be a big contributor along with ingested stimulants, both natural and manmade. The muscles of mastication work in conjunction with many other head and neck muscles to provide the needed jaw movements for eating, drinking, speaking, laughing, crying, and frowning—just to mention a few. Present day occlusal guards seem to be protecting the teeth but overworking the musculature of mastication and in turn affecting many other muscles in the head and neck.

There are many known devices that are used to treat Bruxism. Essentially, the present state of the art for occlusal guards is that they provide an interface of hard plastic that the teeth (controlled by the muscles, and at night time this control is involuntary and uninhibited especially during dreaming) can "skate" around on and supposedly provide some freedom for the excessive muscular activity. The problem is that the muscle activity may actually be increased and these appliances may be triggering and enhancing muscle over activity. There seems to be a familiarity or "stomping ground" or a muscle memory "sweet spot" or "planes" that encourage more habitual and parafunctional muscle activity.

The hard interface unfortunately creates an end point or familiar home for the muscle driven teeth to teeth match-up and subsequently the recurrence of these contacts becomes more comfortable than desirable. These types of brux guards do little if any to minimize muscle activity.

The cuspid disclucing appliances utilize a hard contact for interfacing between the opposing dental arches. This contact, incline, or ramp, is used to restore, correct, manage, or create the "cuspid protected appliance" and they do just that. However there is little or no reduction of the muscle activity.

Another popular appliance known as the NTI (nociocептive trigemeinal inhibition) utilizes a hard interface between opposing dental arches in the form of an anterior deprogramming device to supposedly reduce muscle activity. It is reported to reduce parafunctional muscular activity during sleep while also disengaging ones teeth. These guards are still bulky and obtrusive and are not recommended for any wear during waking hours.

Other appliances utilizing hard interfaces use different "group function" principles to dissipate or moderate the interocclusal forces from parafunctional muscular activity during sleep. Again, none of these appliances appreciably reduce the muscular activity.

Still other appliances, some of which are soft, attempt to interface the teeth to teeth contact during the parafunctional muscular activity, however they are designed as a soft interface between all the opposing posterior teeth resulting in a mere cushioning of the parafunctional activity. This is the case in the over the counter-home remedy "boil and bite" type of mouth guard. These appliances are bulky and do not fit comfortably. The excessive opening of the vertical dimension and interference with the free-way space is damaging to the temporal mandibular joint (TMJ or jaw joint). These devices encourage excessive muscular activity much like having chewing gum in one's mouth. Covering posterior teeth, whether with soft or hard material, will incite muscular activity and place undue stress on the jaw joint.

Besides the above mentioned shortcomings practically all occlusal guards require a commercial laboratory to be involved increasing the cost to the patient. Most are typically cumbersome and difficult to wear and hence many practitioners are reluctant to "sell" their patients a relatively costly device which they may not be able to regularly wear. The resulting potential for buyer's remorse is too high for most dental practitioners to enthusiastically encourage their patient base to accept. Upon merely seeing a model of a proposed, traditional type, occlusal guard, most patients immediately tend to deny their need for such treatment knowing all too well they will not be able to tolerate such a device.

Estimates indicate that more than 85% of the general adult population (potentially more if considering affected children) are experiencing signs and or symptoms of bruxism. Dental professionals can easily see and verify the damaging effects of this malady; however, the insidious nature of this condition is such that most patients are totally unaware of the problem. Daytime parafunctional habits are most often denied by patients simply because of the habitual nature of the process. Much like blinking where one has voluntary control over eyelid closure, daytime habits of clenching go completely unnoticed. Most patients have no realization of either daytime or nighttime bruxism. Rarely does a patient report to his dental practitioner that he has been clenching during sleep, yet many signs and symptoms are apparent to the observant practitioner.

Unfortunately, it is generally very difficult to convince patients that they have a bruxism problem.

II. SUMMARY OF THE INVENTION

This invention is a dental appliance designed to treat bruxism during sleep and bruxism and other related parafunctional habits during waking hours. The daytime use of this appliance is directed towards creation of a mindfulness or awareness of any related habits as opposed to using the device as a "punching bag" for release of tension etc. The sleep time wear is designed to protect natural teeth and all dental work from the damage of the somewhat uninhibited forces of bruxism during sleep.

This invention is a dental appliance that utilizes the natural occurring phenomenon known as "canine disclusion, or canine guidance, or cuspid protected occlusion" that has been recognized in dentistry and orthodontics practically since the beginning of these professions. Canine disclusion is a principle used for practically all orthodontic cases and practically all dental reconstruction cases. It is also the principle that a majority of all occlusal guards have utilized in the past. It is the phenomenon where the opposing canines interact to disengage and protect front and back teeth from excessive wear as the patient goes from maximum inter-cuspation (when upper and lower teeth are fully interdigitated whereas respective cusp tips of upper and lower teeth are completely seated into the respective fossae of their opposing teeth) to a lateral position (lateral or protrusive excursion) while chewing. This phenomenon allows the crushing forces of mastication to occur in the maximum intercuspation position but disengages the cuspids as lateral movements occur (similar in some respects to a cow chewing its cud in a lateral manner) which protects the human teeth from damaging lateral forces.

This appliance utilizes these principles but in a completely different manner. It is completely soft and the discluding principle is a misguiding element and not a guiding one.

The nature of this invention and its presentation as a "front tooth protector" is able to overcome the inherent "refusal to accept the problem" of the traditional treatments. As patients see and realize that they could actually wear this device nightly they tend to "accept" the treatment. The most effective means of patient education appears to be a co-diagnosis whereas the patient discovers the associated tooth wear with the practitioner's help. Having noticed the apparent wear of any of the cuspids (remember nature's cuspid disclusion is working to protect the teeth but not really eliminating the muscle activity) the dental practitioner gives the patient a good sized face mirror and asks the patient to approximate the cuspids as they if they fit as a puzzle. This happens almost automatically. The patient is instructed to hold that pose and together they discuss the wear. Young and old, it is practically always evident. Most often this puzzle will be evident on all four cuspids and usually also on the patient's anterior teeth. Capturing this "puzzle picture" as a digital image serves extremely well as a motivational tool when professionals make treatment recommendations and also provides an excellent documentation of the malady.

According to one embodiment of this invention, a dental appliance may comprise: a body comprising a front wall, a back wall, and a top connecting the front wall to the back wall. The body may define: four incisor reception zones suitable to receive four juxtaposed associated incisor teeth on a lower jaw; a first canine reception zone suitable to receive a first associated canine tooth that is juxtaposed to a first end of the incisor teeth; and, a second canine reception zone suitable to receive a second associated canine tooth that is juxtaposed to a second end of the associated incisor teeth. The portion of the top of the body that defines the four incisor reception zones may have a first thickness T1, the portion of the top of the body that defines the first canine reception zone may be elastic and may have a second thickness T2, and the portion of the top of the body that defines the second canine reception zone may be elastic and may have a third thickness T3. The second thickness T2 and the third thickness T3 may be significantly greater than the first thickness T1.

According to another embodiment of this invention, a dental appliance may comprise: a body comprising a front wall, a back wall, and a top connecting the front wall to the back wall. The body may define: an incisor reception zone suitable to receive a plurality of juxtaposed associated incisor teeth, a first canine reception zone suitable to receive a first associated canine tooth that is juxtaposed to a first end of the incisor teeth, and, a second canine reception zone suitable to receive a second associated canine tooth that is juxtaposed to a second end of the associated incisor teeth. The portion of the top of the body that defines the incisor reception zone may have a first thickness T1, the portion of the top of the body that defines the first canine reception zone may have a second thickness T2, and the portion of the top of the body that defines the second canine reception zone may have a third thickness T3. The second thickness T2 and the third thickness T3 may be significantly greater than the first thickness T1.

According to yet another embodiment of this invention, a method may comprise the steps of: (A) providing a patient having: a plurality of juxtaposed incisor teeth; a first canine tooth juxtaposed to a first end of the plurality of incisor teeth; and, a second canine tooth juxtaposed to a second end of the plurality of incisor teeth; (B) determining that the patient has bruxism; (C) fabricating a dental appliance for the patient to treat the bruxism, the dental appliance comprising: a body comprising a front wall, a back wall, and a top connecting the front wall to the back wall, the body defining: an incisor reception zone suitable to receive the plurality of juxtaposed incisor teeth; a first canine reception zone suitable to receive the first canine tooth; a second canine reception zone suitable to receive the second canine tooth; wherein the portion of the top of the body that defines the incisor reception zone has a first thickness T1; wherein the portion of the top of the body that defines the first canine reception zone has a second thickness T2; wherein the portion of the top of the body that defines the second canine reception zone has a third thickness T3; and, wherein T2 and T3 are significantly greater than T1; and, (D) wearing the dental appliance on the incisor teeth and the first and second canine teeth to treat the bruxism.

One advantage of this invention is, a dental appliance may include making a diagnosis of tooth damaging maladies quickly and easily.

Another advantage of this invention is, a dental appliance may comprise of a co-diagnosis almost instantaneously.

Another advantage of this invention is, a dental appliance may comprise of a formulation easily designed to each specific patient and may be accomplished by entry level personnel.

Another advantage of this invention is, a dental appliance may comprise of a small appliance worn easily and extremely comfortable day or night.

Another advantage of this invention is, a dental appliance may comprise of a device easily made in the dental office, without sophisticated laboratory equipment reducing costs in a short period of time.

Still another advantage of this invention is, a dental appliance may comprise of a device easily made by entry level dental personnel.

Still another advantage of this invention is, a dental appliance may be readily accepted by patients since "puzzle picture" enlightens patient to excessive tooth wear almost instantly.

Still another advantage of this invention is, a dental appliance may comprise of a body that minimally opens the patients vertical dimension of occlusion and hence is extremely comfortable.

Still another advantage of this invention is, a dental appliance may be worn even by those wearing the CPAP machines.

Yet another advantage of this invention is, a dental appliance may be worn over any type of dental appliance including implant supported dentistry of all types.

Yet another advantage of this invention is, a dental appliance may require only the smallest, single, lower impression (capturing the essence of only the lower front eight teeth).

Yet another advantage of this invention is, a dental appliance may be that it can be worn inconspicuously during daytime.

Yet another advantage of this invention is, a dental appliance may provide potential for wear by young children and adolescents.

Yet another advantage of this invention is, a dental appliance may provide for potential for wear by some requiring anti snore devices.

Additional benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF THE INVENTION

Figure 1:
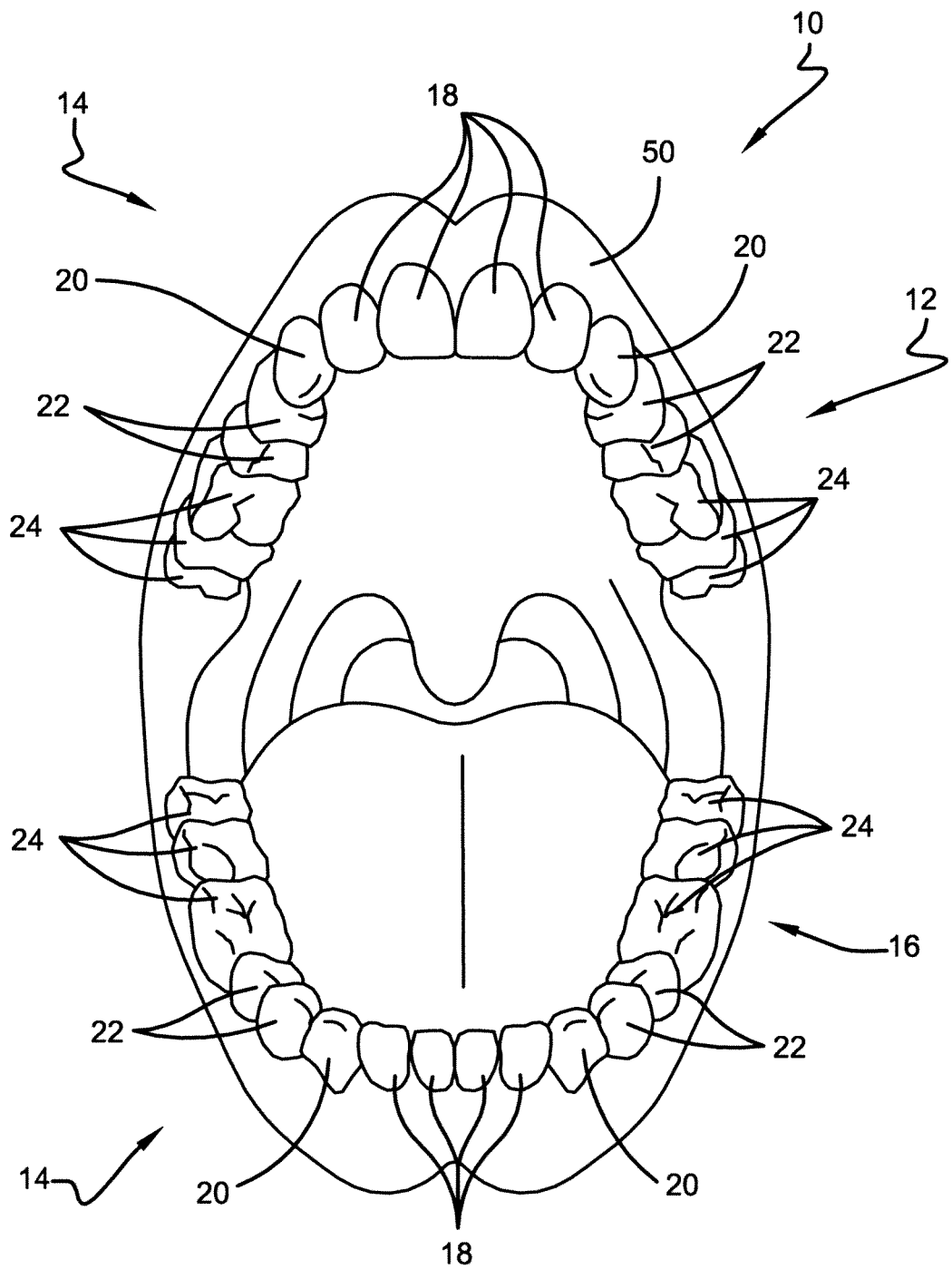
FIG. 1 is a front perspective view of a human mouth.
Figure 2:
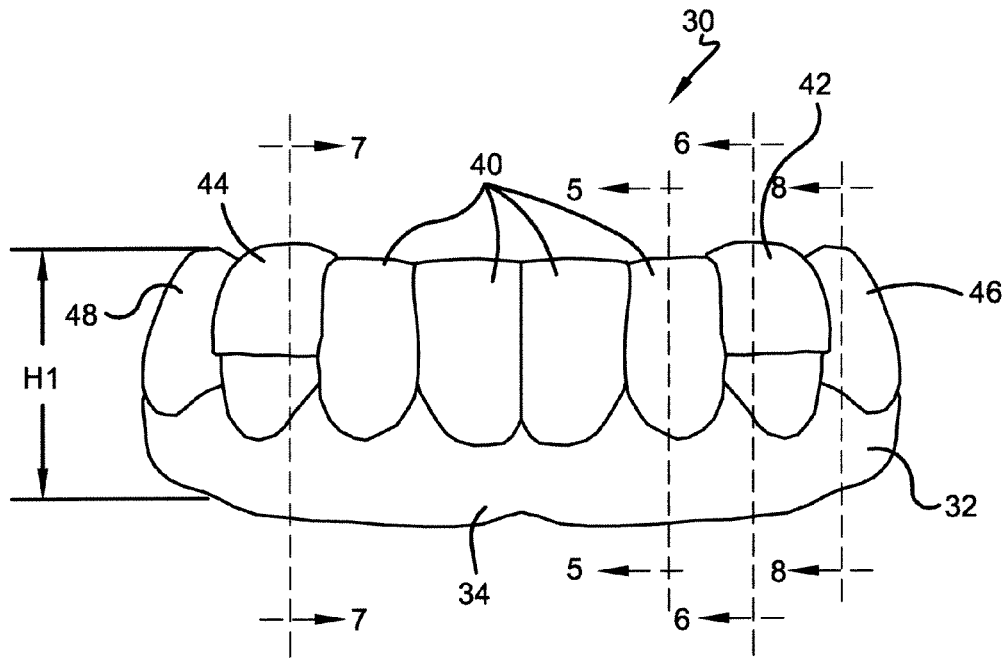
FIG. 2 is a front view of a dental appliance.
Figure 3:
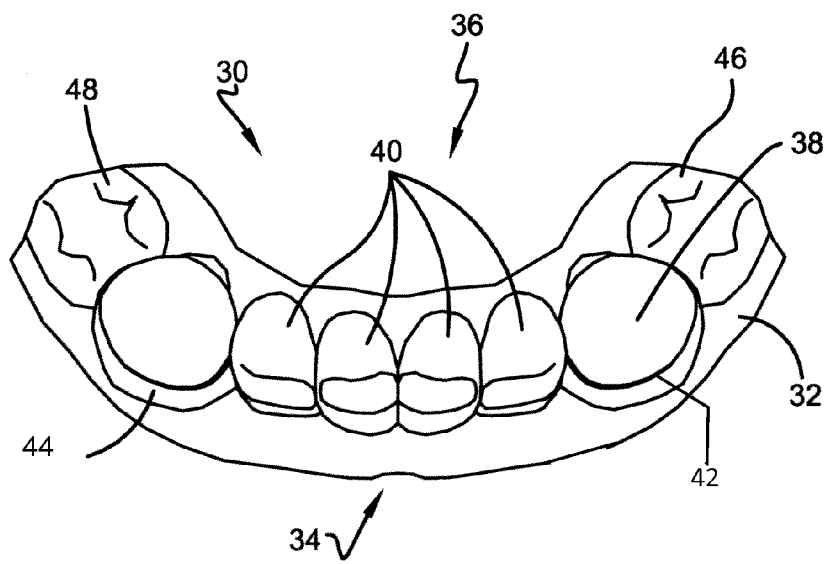
FIG. 3 is a top view of the dental appliance shown in FIG. 2.
Figure 4:
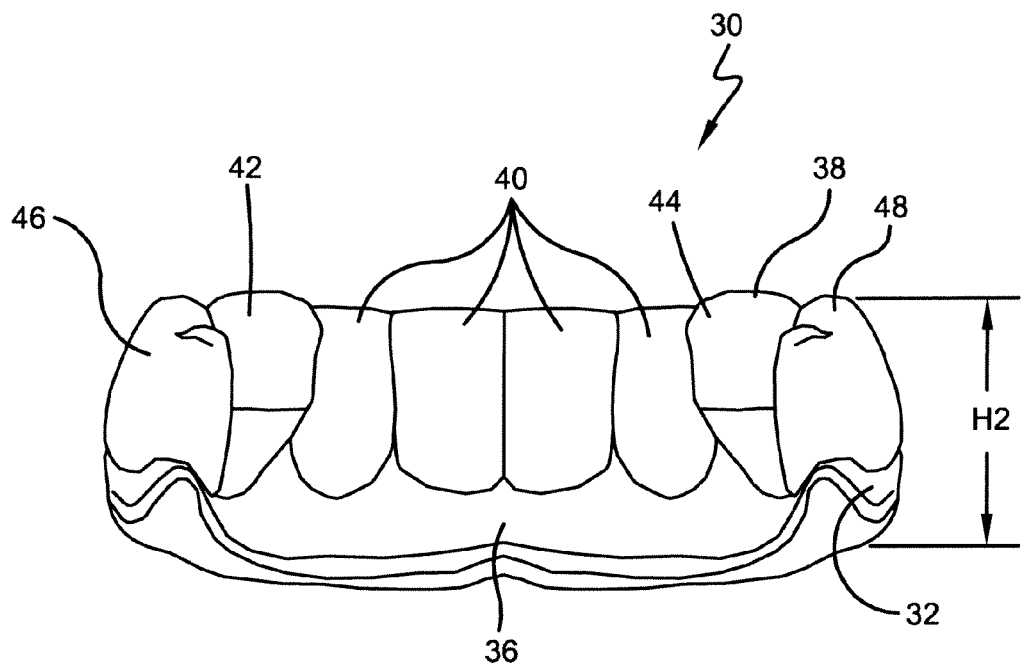
FIG. 4 is a back view of the dental appliance shown in FIG. 2.
Figure 5:
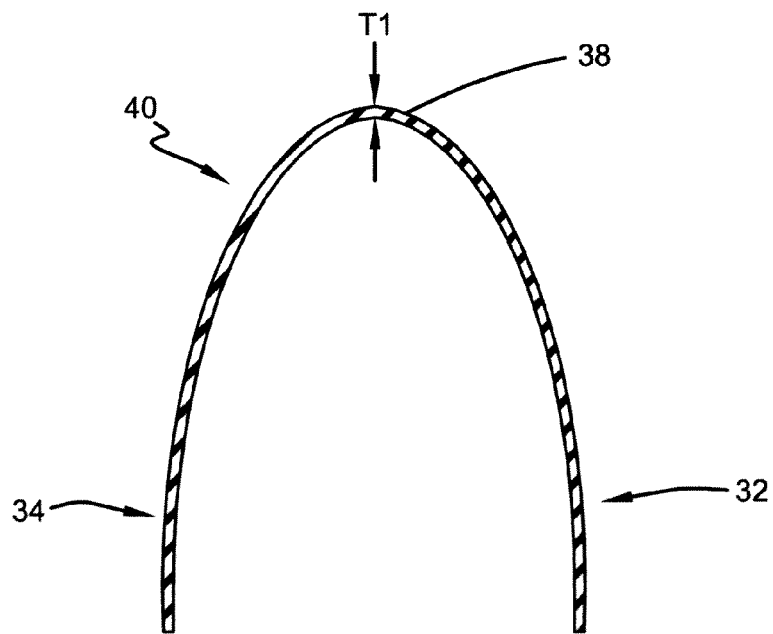
FIG. 5 is a sectional view taken through line 5-5 in FIG. 2.
Figure 6:
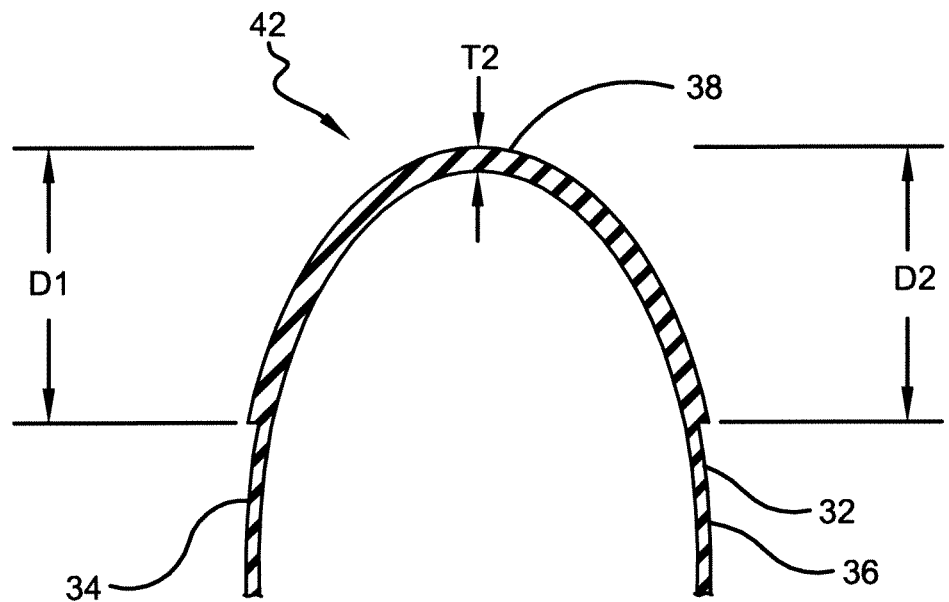
FIG. 6 is a sectional view taken through line 6-6 in FIG. 2.
Figure 7:
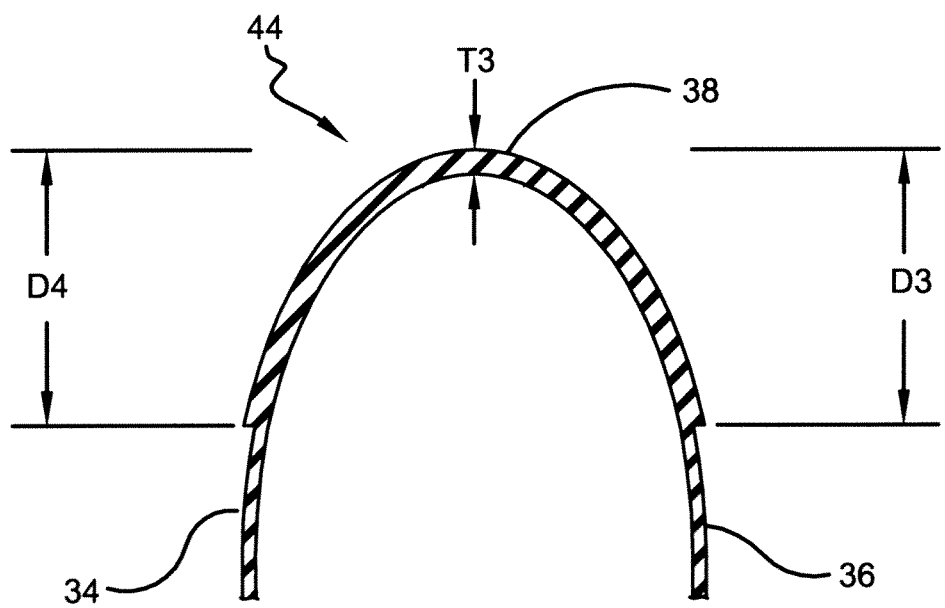
FIG. 7 is a sectional view taken through line 7-7 in FIG. 2.
Figure 8:
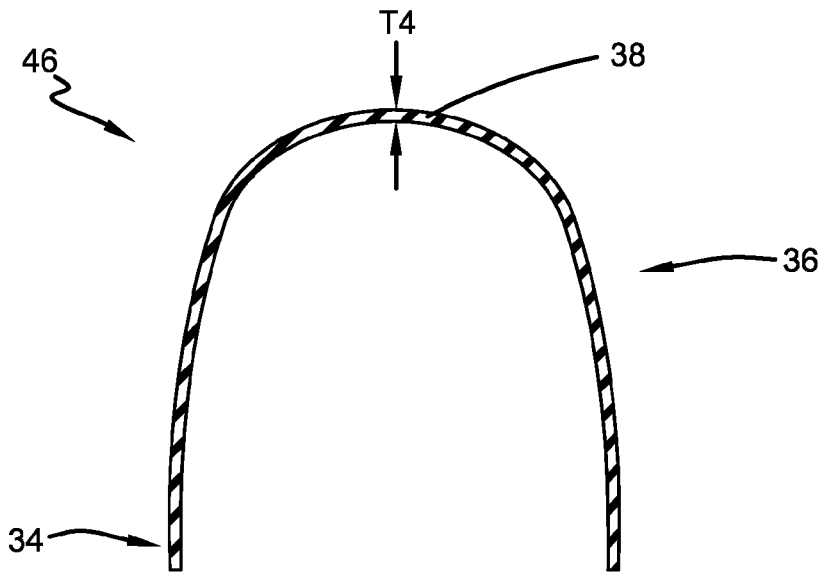
FIG. 8 is a sectional view taken through line 8-8 in FIG. 2.

Referring now to the drawings wherein the showings are for purposes of illustrating embodiments of the invention only and not for purposes of limiting the same, and wherein like reference numerals are understood to refer to like components, FIG. 1 shows a typical human mouth 10 that may use a dental appliance 30, shown in FIGS. 2-4, according to embodiments of this invention. The mouth 10 may include an upper jaw 12 having teeth 14 and a lower jaw 16 having teeth 14. More specifically, the teeth 14 for each jaw 12, 16 comprise four incisors 18, two canines (also called cuspids) 20, two premolars 22 and six molars 24. The teeth 14 may extend from dental alveolus 50 as is known to those of skill in the art.

With reference now to FIGS. 1-4, the dental appliance 30 that may be used to treat bruxism may include a body 32 comprising a front wall 34, a back wall 36, and a top 38 connecting the front wall 34 to the back wall 36. The body 32 may define teeth reception zones. Specifically, the body 32 may define an incisor reception zone 40 that is suitable to receive a plurality of juxtaposed incisor teeth 18, four shown, a first canine reception zone 42 suitable to receive a first canine tooth 20 that is juxtaposed to a first end of the incisor teeth 18, and a second canine reception zone 44 suitable to receive a second canine tooth 20 that is juxtaposed to a second end of the incisor teeth 18. In one embodiment, the incisor and first and second canine reception zones 40, 42, 44 are sufficient to maintain the dental appliance 30 in place on the teeth 14. In another embodiment, additional teeth reception zones may be used. In a specific embodiment, a first premolar reception zone 44 suitable to receive a first premolar tooth 22 that is juxtaposed to the first canine tooth 20 and a second premolar reception zone 48 suitable to receive a second premolar tooth 22 that is juxtaposed to the second canine tooth 20 may be used. As shown in FIG. 3, the body 32 may receive only the incisor teeth 18, the canine teeth 20 and the premolar teeth 22.

With reference now to FIGS. 2-8, the portion of the top 38 of the body 32 that defines the incisor reception zone 40 may have a first thickness T1; the portion of the top 38 of the body 32 that defines the first canine reception zone 42 may have a second thickness T2; and, the portion of the top 38 of the body 32 that defines the second canine reception zone may have a third thickness T3. In one embodiment, the second thickness T2 and the third thickness T3 are significantly greater than the first thickness T1. In this way, the canine reception zones 42, 44 extend vertically higher than the remaining portions of the dental appliance 30 and only the canine reception zones 42, 44 are used to slightly open the vertical dimension of maximum intercuspation. In one embodiment, the first thickness T1 is between 0.25 millimeters and 0.75 millimeters inclusively and the second and third thicknesses T2, T3 are between 0.75 millimeters and 1.5 millimeters inclusively. In one embodiment the second and third thicknesses T2, T3 are substantially the same. The portions of the top 38 of the body 32 that define the first and second premolar reception zones 46, 48 may each have a fourth thickness T4. The fourth thickness T4 may be significantly less than the second and third thicknesses T2 and T3. In one embodiment, the fourth thickness T4 is between 0.25 millimeters and 0.75 millimeters inclusively. In one embodiment the first thickness T1 and the fourth thickness T4 are substantially the same. In one embodiment, the entire dental appliance 30 has the first thickness T1 (thus T4 equals T1) except the second and third thicknesses T2, T3.

With reference now to FIGS. 1-4, the dental appliance 30 may be formed of any material and in any manner chosen with the sound judgment of a person of skill in the art. In one embodiment, the portions of the top 38 of the body 32 that define the first and second canine reception zones 42, 44 are elastic. In this way, when opposing canines 20, 20 (one from the upper jaw 12 and the other from the lower jaw 16) contact each other, the impact is a soft "no end point" relationship. The effect is one of a disconcerting effect on muscle habits in the patient. This is opposed to known hard surface (non-elastic) occlusal guards which permit the patient's musculature to become continuously familiar with the occlusal guard surface interface and do nothing more than interface between opposing teeth. When the canine reception zones 42, 44 are elastic, however, the muscle memory is interrupted and bruxism activity is subdued. In one embodiment, the canine reception zones 42, 44 are formed of a relatively soft plastic. In one specific embodiment, the canine reception zones 42, 44 are formed of ethylene vinyl acetate (EVA). In yet another embodiment, the entire dental appliance 30 is formed of EVA.

With reference now to FIGS. 1-8, in one embodiment, the dental appliance 30 is fitted to the teeth 14 of the upper jaw 12. In another embodiment, the dental appliance 30 is fitted to the teeth 14 of the lower jaw 16. Fitting the dental appliance 30 to the teeth 14 of the lower jaw 16 has the advantage of using gravity to help maintain the dental appliance 30 in place. Another advantage of fitting the dental appliance 30 to the teeth 14 of the lower jaw 16 is that the proprioception of the lower jaw 16 canines 20 differ from that of the upper jaw 12 canines 20—primarily because of the mobile nature of the mandible relative to the stationary position of the maxilla. The front wall 34 of the dental appliance 30 may have a height H1 and the back wall 36 may have a height H2. In one embodiment, the heights H1, H2 are sufficient to cover the teeth 14 but no more. In another embodiment, shown, the heights H1, H2 are sufficient to cover the teeth 14 and to at least partially cover the dental alveolus 50 from which the teeth 14 extend (this can be seen by observing the portion of the dental appliance 30 that extends below the various tooth reception zones 40, 42, 44, 46, 48). The portions of the first and second canine reception zones 42, 44 that have the second and third thickness T2, T3, respectively, may be sized and shaped in any manner chosen with the sound judgment of a person of skill in the art. In one embodiment, the portion of the first canine reception zone 42 that has the second thickness T2 may extend, as shown, entirely across the width W1 of the first canine reception zone 42 and a distance D1 of at least 3.0 millimeters down the front wall 34 and a distance D2 of at least 3.0 millimeters down the back wall 36. Similarly, the portion of the second canine reception zone 44 that has the third thickness T3 may extend, as shown, entirely across the width W2 of the second canine reception zone 44 and a distance D3 of at least 3.0 millimeters down the front wall 34 and a distance D4 of at least 3.0 millimeters down the back wall 36. In another embodiment, the distances D1, D2, D3 and D4 are about 5.0 millimeters.

With reference now to FIGS. 2-3 and 10-12, in another embodiment a dental appliance 60 that may be used to treat bruxism may be similar to the previously described dental appliance 30. However, for this embodiment a middle portion of the front wall 34 is removed. In this way, one or more of the incisor teeth 18 (four shown) are not covered by the dental appliance 60 and thus may be visible even when the dental appliance 60 is being worn. This may make it easier for the patient to wear the dental appliance 60 during the day. In yet another embodiment, not shown, a middle portion of the back wall 36 is removed.

With reference now to FIGS. 2-3 and 13-14, in yet another embodiment a dental appliance 70 that may be used to treat bruxism may be similar to the previously described dental appliance 30. However, for this embodiment the dental appliance 70 has two separate parts or sections 72, 74. For the specific embodiment shown, each section 72, 74 covers one canine 20 and one neighboring premolar 22. In another specific embodiment, now shown, each section 72, 74 covers one canine 20 and one neighboring incisor 18. In yet another specific embodiment, not shown, each section 72, 74 covers one canine 20, one neighboring premolar 22, and one neighboring incisor 18 (three teeth total). In still another specific embodiment, not shown, each section 72, 74 covers only one canine 20.

Figure 9:
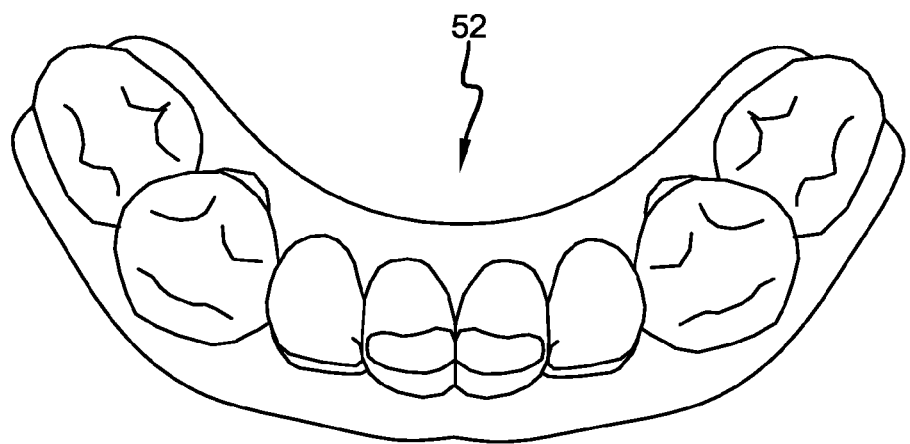
FIG. 9 is a top view of a model.
Figure 10:
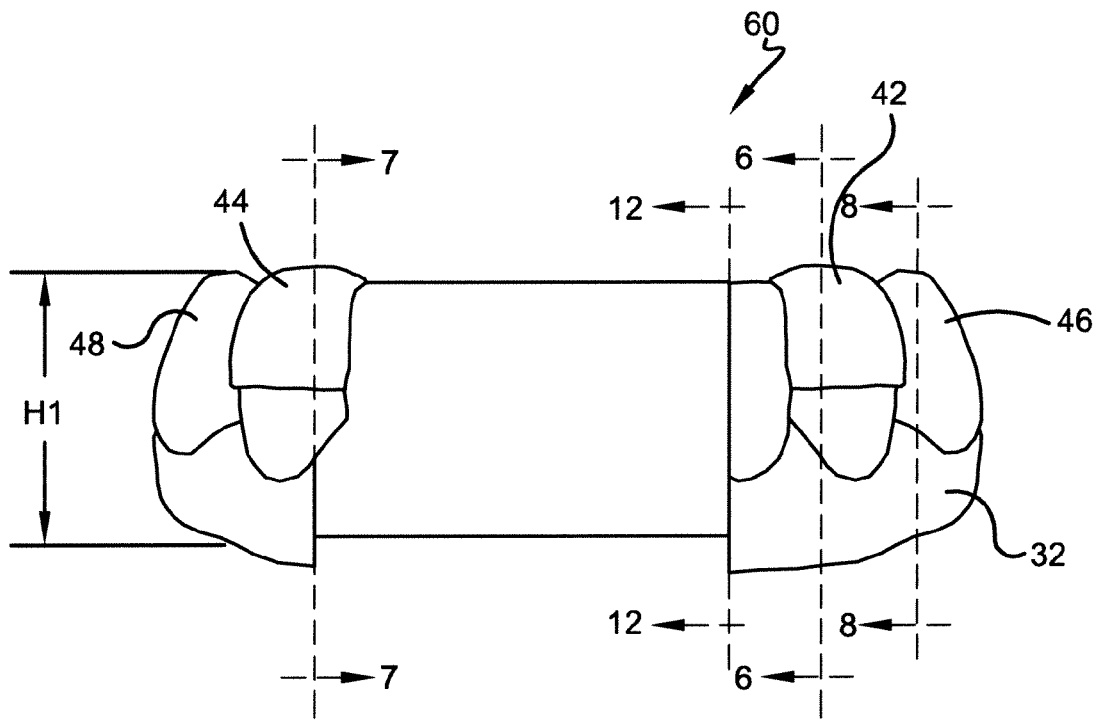
FIG. 10 is a front view of a dental appliance according to another embodiment.
Figure 11:
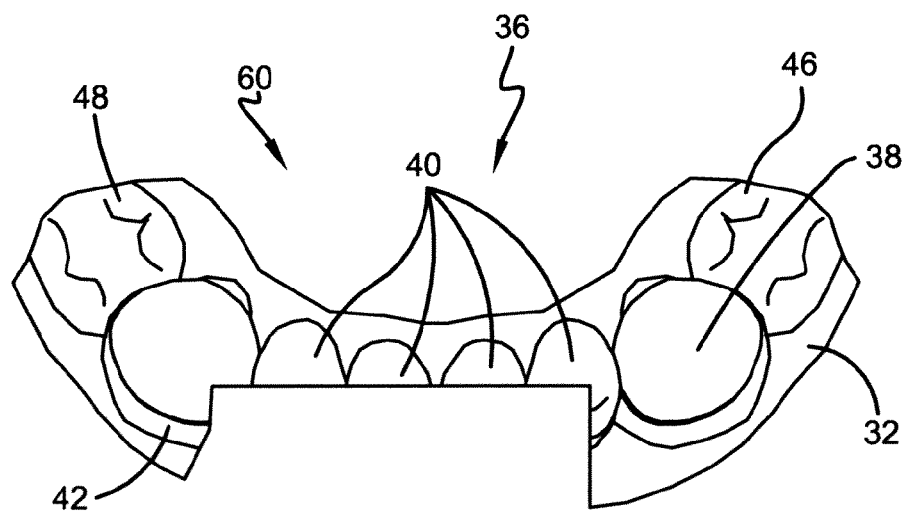
FIG. 11 is a top view of the dental appliance shown in FIG. 10.
Figure 12:
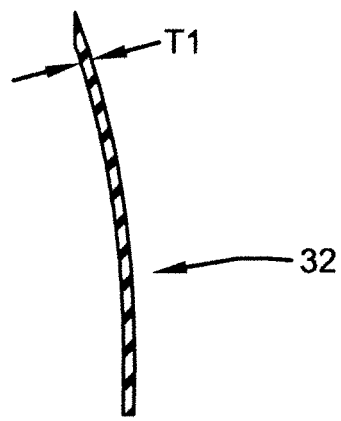
FIG. 12 is a sectional view taken through line 12-12 in FIG. 10.
Figure 13:
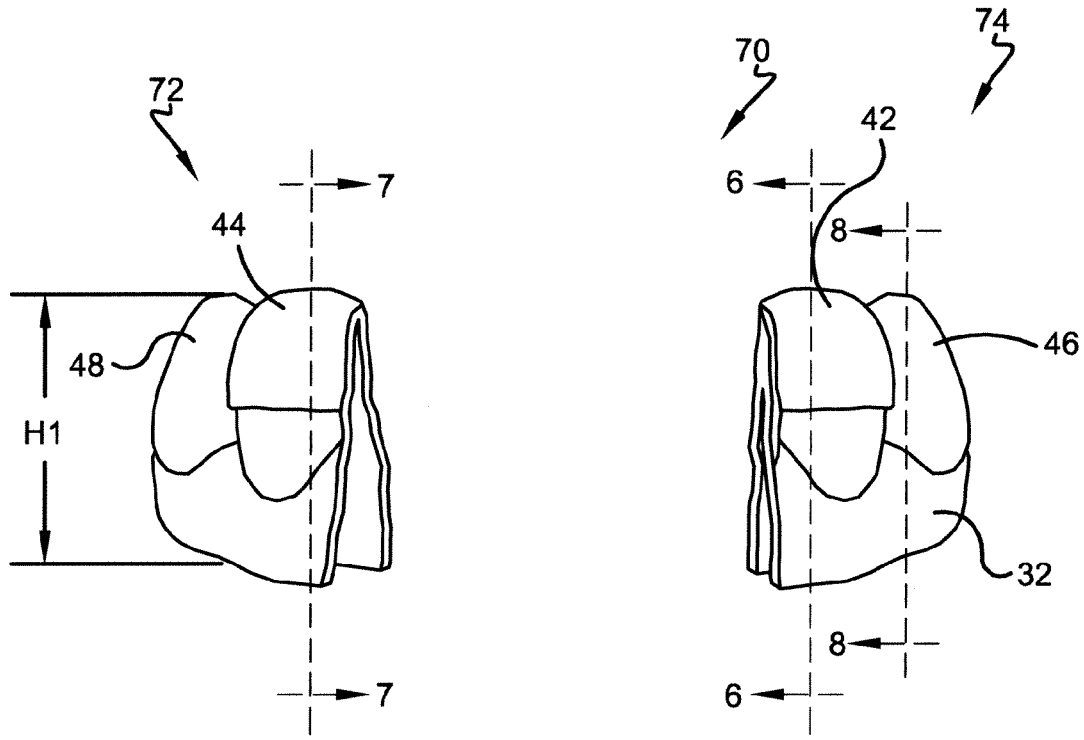
FIG. 13 is a front view of a dental appliance according to yet another embodiment.
Figure 14:
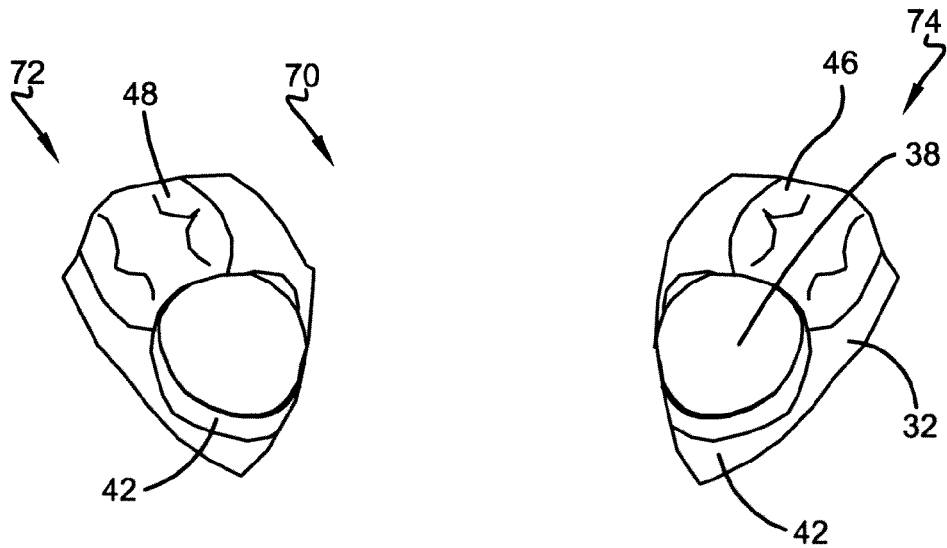
FIG. 14 is a top view of e dental appliance shown in FIG. 13.

With reference now to all the FIGURES, the fabrication and use of the dental appliance 30, 60, 70 will now be described. First, it may be determined that the patient has bruxism. This determination may, of course, be made by a dental practitioner. However, a co-diagnoses (with the patient) is beneficial as the patient is then more likely to accept the required treatment. In one specific embodiment, a reflective surface such as a mirror may be used to show the patient the wear status of the patent's teeth. The most obvious worn enamel (usually on one or more front teeth) is easily seen by the patient forming a "puzzle picture" for the patient. This wear status may be shown to the patient on a monitor and a picture may be taken of the wear status, such as by a digital camera. The patient may then be shown an example dental appliance to allay any fears of wearing the dental appliance 30, 60, 70. The dental practitioner may also explain the benefits of using the dental appliance 30, 60, 70 including muscle relaxation verses muscle tension, daytime mindfulness exercises using the dental appliance 30, 60, 70, reduction in cracked teeth and the fact that all dental work will last longer when protected from the forces of bruxism. Once the patient decides that the dental appliance 30, 60, 70 will be beneficial, the dental practitioner can then fabricate it. To do this, the dental practitioner may first determine the required thicknesses for the dental appliance 30, 60, 70 using the puzzle picture. Next, the dental practitioner may make a relatively small impression of the anterior quadrant of the patient's teeth with an alginate material. A model, such as model 52 shown in FIG. 9, is then made from the impression. The dental appliance 30, 60, 70 may then be vacuum formed, trimmed, and then delivered to the patient, custom made, immediately. It can be formed of any thickness and in any color or combination of colors chosen with the sound judgment of a person of skill in the art.

With continuing reference to all the FIGURES, once the dental appliance 30, 60, 70 is made and delivered, the patent then wears it. The dental appliance 30, 60, 70 is held in place via a hydro-seal, similar to how dentures remain in place The patent may wear the dental appliance 30, 60, 70 during sleep time to protect the patient from damage caused by bruxism. The patient may also wear the dental appliance 30, 60, 70 during wake time to create awareness in the patient of any bruxism related habits. Applicant has discovered that for many patients, wearing the dental appliance 30, 60, 70 at night may be more important than wearing it during sleep time. As noted above, wearing the dental appliance 30, 60, 70 will disconcert muscle memory in the patient and thus will help train the patient's muscles not to grind and the like. Wearing the dental appliance 30, 60, 70 will help in providing relief for the patient from: head, neck, and shoulder muscular tension and the potentially associated sleep apnea, headaches, migraine triggers, neckaches, and shoulder aches. Applicant has discovered that for some patients wearing the dental appliance 30, 60, 70 works effectively in reducing or eliminating snoring. Wearing the dental appliance 30, 60, 70 will also help minimize dental pain, tooth thermal and tactile sensitivity, enamel abfractions and abrasions. These signs and symptoms can be treated during the day when they arise from conscious, habitual, parafunctional clenching, grinding, gnashing and bracing of one's teeth. In this case, the dental appliance 30, 60, 70 provides mindfulness for the patient which is a therapeutic approach to help attenuate the daytime tension and conscious clenching. The same signs and symptoms can also be treated at night when they arise from similar but unconscious activities. Wearing the dental appliance 30, 60, 70 also may protect the patient's teeth from germs and the like thereby protecting the teeth from tooth decay.

Numerous embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

I claim:

1. A method comprising the steps of:
    (A) providing a patient having: a plurality of juxtaposed incisor teeth; a first canine tooth juxtaposed to a first end of the plurality of incisor teeth; and, a second canine tooth juxtaposed to a second end of the plurality of incisor teeth;
    (B) determining that the patient has bruxism;
    (C) fabricating a dental appliance for the patient to treat the bruxism, the dental appliance comprising: a body comprising a front wall, a back wall, and a top connecting the front wall to the back wall, the body defining: an incisor reception zone suitable to receive the plurality of juxtaposed incisor teeth; a first canine reception zone suitable to receive the first canine tooth; a second canine reception zone suitable to receive the second canine tooth; wherein the portion of the top of the body that defines the incisor reception zone has a first thickness T1; wherein the portion of the top of the body that defines the first canine reception zone has a second thickness T2; wherein the portion of the top of the body that defines the second canine reception zone has a third thickness T3; and, wherein T2 and T3 are significantly greater than T1;

(D) wearing the dental appliance on the incisor teeth and the first and second canine teeth to treat the bruxism.

2. The method of claim 1 wherein:
step (A) comprises the step of: providing the patient with: (1) an upper jaw with upper teeth comprising: a plurality of juxtaposed incisor teeth; a first canine tooth juxtaposed to a first end of the plurality of incisor teeth; and, a second canine tooth juxtaposed to a second end of the plurality of incisor teeth; and, (2) a lower jaw with lower teeth comprising: the plurality of juxtaposed incisor teeth; the first canine tooth and the second canine tooth;
step (C) comprises the step of: fabricating the dental appliance wherein the portion of the top of the body that defines the first canine reception zone is elastic and wherein the portion of the top of the body that defines the second canine reception zone is elastic; and,
step (D) comprises the step of: wearing the dental appliance on the incisor teeth and the first and second canine teeth of the lower jaw.

3. The method of claim 2 wherein step (C) comprises the steps of:
making an impression of the incisor teeth and the first and second canine teeth with an alginate material;
making a model of the incisor teeth and the first and second canine teeth from the impression; and,
fabricating the dental appliance of a relatively soft plastic from the model.

4. The method of claim 2 wherein step (D) comprises the steps of:
wearing the dental appliance during sleep time to protect the patient from damage caused by bruxism; and,
wearing the dental appliance during wake time to create an awareness in the patient of any bruxism related habits.

5. The method of claim 2 wherein step (B) comprises the steps of:
using a dental practitioner to determine that the patient has bruxism;
using a reflective surface to show the patient the wear status of the first and second canines of the upper jaw and the first and second canines of the lower jaw so the patient also determines that the patient has bruxism; and,
taking a picture of the wear status.

6. The method of claim 2 wherein step (D) comprises the step of:
disconcerting muscle memory in the patient.

7. A dental appliance comprising:
a body comprising a front wall, a back wall, and a top connecting the front wall to the back wall, the body defining:
an incisor reception zone suitable to receive a plurality of juxtaposed associated incisor teeth;
a first canine reception zone suitable to receive a first associated canine tooth that is juxtaposed to a first end of the incisor teeth;
a second canine reception zone suitable to receive a second associated canine tooth that is juxtaposed to a second end of the associated incisor teeth;
wherein the portion of the top of the body that defines the incisor reception zone has a first thickness T1;
wherein the portion of the top of the body that defines the first canine reception zone has a second thickness T2;
wherein the portion of the top of the body that defines the second canine reception zone has a third thickness T3; and,
wherein the second thickness T2 and the third thickness T3 are significantly greater than the first thickness T1.

8. The dental appliance of claim 7 wherein the body defines:
a first premolar reception zone suitable to receive a first associated premolar tooth that is juxtaposed to the first associated canine tooth;
a second premolar reception zone suitable to receive a second associated premolar tooth that is juxtaposed to the second associated canine tooth; and,
wherein the portions of the top of the body that define the first and second premolar reception zones each have a fourth thickness T4 that is significantly less than the second and third thicknesses T2 and T3.

9. The dental appliance of claim 7 wherein the incisor reception zone is suitable to receive the plurality of juxtaposed associated incisor teeth on an associated lower jaw.

10. The dental appliance of claim 7 wherein:
the portion of the top of the body that defines the first canine reception zone is elastic; and,
the portion of the top of the body that defines the second canine reception zone is elastic.

11. The dental appliance of claim 7 wherein the body is formed of ethylene vinyl acetate.

12. The dental appliance of claim 7 wherein the second and third thicknesses T2 and T3 are not greater than 1.5 millimeters.

13. The dental appliance of claim 7 wherein the front and back walls are high enough to completely cover the four associated incisor teeth and the first and second associated canine teeth and to partially cover associated dental alveolus from which the associated four incisor teeth and the associated first and second canine teeth extend.

14. The dental appliance of claim 7 wherein:
the portion of the first canine reception zone that has the second thickness T2 extends: (1) entirely across the width of the first canine reception zone; (2) at least 3.0 millimeters down the front wall; and, (3) at least 3.0 millimeters down the back wall; and,
the portion of the second canine reception zone that has the third thickness T3 extends: (1) entirely across the width of the second canine reception zone; (2) at least 3.0 millimeters down the front wall; and, (3) at least 3.0 millimeters down the back wall.

* * * * *